(12) United States Patent
Roth

(10) Patent No.: US 8,267,977 B2
(45) Date of Patent: Sep. 18, 2012

(54) CANULATED TITANIUM IMPLANT FOR CORRECTING FLAT FEET IN CHILDREN

(75) Inventor: Sandor Roth, Rijeka (HR)

(73) Assignee: Sandor Roth, Šilo (HR)

( * ) Notice: Subject to any disclaimer, the term of this patent is extended or adjusted under 35 U.S.C. 154(b) by 1160 days.

(21) Appl. No.: 11/887,258

(22) PCT Filed: Mar. 20, 2006

(86) PCT No.: PCT/HR2006/000005
§ 371 (c)(1),
(2), (4) Date: Sep. 27, 2007

(87) PCT Pub. No.: WO2006/103481
PCT Pub. Date: Oct. 5, 2006

(65) Prior Publication Data
US 2009/0082818 A1    Mar. 26, 2009

(30) Foreign Application Priority Data

Mar. 29, 2005   (HR) .............................. P 20050295 A

(51) Int. Cl.
*A61B 17/04*   (2006.01)
(52) U.S. Cl. ........................................ 606/304; 606/301
(58) Field of Classification Search ............... 606/67, 606/68, 300–331, 60, 246–279; 411/378–426
See application file for complete search history.

(56) References Cited

U.S. PATENT DOCUMENTS

| | | | | |
|---|---|---|---|---|
| 5,360,450 A * | 11/1994 | Giannini | ........ | 623/21.19 |
| 5,868,749 A * | 2/1999 | Reed | ........ | 606/76 |
| 5,871,486 A * | 2/1999 | Huebner et al. | ........ | 606/305 |
| 6,306,140 B1 * | 10/2001 | Siddiqui | ........ | 606/315 |
| 6,319,254 B1 * | 11/2001 | Giet et al. | ........ | 606/916 |
| 6,402,757 B1 * | 6/2002 | Moore et al. | ........ | 606/80 |
| 6,604,945 B1 * | 8/2003 | Jones | ........ | 433/173 |
| 7,033,398 B2 * | 4/2006 | Graham | ........ | 623/21.18 |
| 7,678,153 B2 * | 3/2010 | Katz et al. | ........ | 623/21.11 |
| 7,708,738 B2 * | 5/2010 | Fourcault et al. | ........ | 606/67 |
| 7,731,738 B2 * | 6/2010 | Jackson et al. | ........ | 606/304 |
| 2003/0028193 A1 * | 2/2003 | Weil et al. | ........ | 606/73 |
| 2004/0068261 A1 * | 4/2004 | Fourcault et al. | ........ | 606/67 |
| 2005/0101961 A1 | 5/2005 | Huebner et al. | | |
| 2005/0251264 A1 | 11/2005 | Katz et al. | | |
| 2006/0200151 A1 * | 9/2006 | Ducharme et al. | ........ | 606/73 |

FOREIGN PATENT DOCUMENTS

EP    0 560 249 A    9/1993
GB    2 355 505 A    4/2001

* cited by examiner

*Primary Examiner* — Kevin T Truong
*Assistant Examiner* — Christopher Beccia

(57) ABSTRACT

The cannulated titanium implant (screw) for correction of flat feet in children characterized by that: a) the diameter of the stem is D=4.8 mm±25%, recommended 4.8 mm±10%, and especially recommended 4.8 mm, b) it is cannulated, whose diameter is C=2 mm+25%, recommended 2 mm±10%, and especially recommended 2 mm, c) the screw-thread height is 1.15 mm±25%, recommended 1/15 mm±10%, and especially recommended 1.15 mm, d) on the point of the screw, which ends at the angle of 90°, on the apex thread are trisect cuts at the angle of 120°. The edges of the apex thread are cut at the angle of 55°. At the very top of the point of the screw, the trisect cuts of the apex thread go inward the tunnel in the length of the screw by 1.5 mm, e) this type of the point replaces the use of the drill and the tapping device.

13 Claims, 4 Drawing Sheets

CANULATED TITANIUM IMPLANT FOR CORRECTING FLAT FEET IN CHILDREN

DESCRIPTION OF THE INVENTION

1. Field of the Invention

This invention was designed for the operative correction of extremely flat feet in children with a heel valgus (Pes planovalgus gr III-IV), which inspite of using all existing physical methods of correction and usage of orthrotics by the age of twelve could not correct the axis of the heel and bring the arch of the foot to a permanent satisfying result.

2. Technical Problem

There have been many years now that one has tried to solve the problem by different surgical methods, but they have up to now demanded operative opening of tarsal bones (by an incision of 30 mm-50 mm), i.e. by opening the operative area to change the relation of tarsal bones (the foot bones), the surrounding tissue needed to be lesioned.

The screw could have been directed in the right position and into the right place by opening the surface of the bone. Therefore, the post-operative recuperation took longer, and in many cases a long-term (several weeks) mobilization was needed.

The second problem was that of the breakage of the inserted screws before the correction of the feet was completed. Removing the remaining bits of the screw resulted in damaging a great deal of the healthy bone.

The third problem was the premature loosening of the screw which should have worked for 30 months (the screws were implanted during that period of time) so that the proper correction of the arch of the foot and the axis of the heel would take place as the feet develop.

The fourth problem was the existing ordinary head of the screw. When removing it per cutem, one needed to use the injection needle to locate the head of the screw for it to be drilled out, which was harder to do. Again, one had to operatively remove the screw, since the head of the screw was in the shape of the ball, which rested on a thin neck, the head of the screw could catch the edge of the heel bone, which definitely was of no advantage.

The fifth problem occurred with the resorptive screw (if such was implanted-so Italian authors), which broke already after six months of its placement, so the long-term correction process of thirty months that is needed, comes into question. According to the Anglo-Saxon authors, this implant is unstable and falls out before the required period of correction is finished. We also do know sufficiently enough of how the material affects the body, it falls apart and is resorbed during the time it was implanted.

The present invented screw solves all these problems by its shape and construction, i.e. it can be inserted through a small skin gap directed by Kirschners's guide-wire (it is canulated 1). The screw's stem/body is much stronger and larger, therefore, a much bigger force is needed for the screw to break, and even if it does break, it can be removed easier with a much lesser lesion of the surrounding tissue. The point of the screw has apex thread 2, which also lessens the lesion of the bone while positioning it. Since the head 3 of the screw is bigger and conical by its shape, and the screw does not have a thin neck at the connection 4 to the screw-thread 14. The screw, as it is positioned, sets into the bone by self-tightening into it. Therefore, it rarely loosens. The screw cannot grow into the bone tissue because it has a conical head 3 and no thin neck between the head 3 of the screw and the screw-thread 14, so it is easier to remove it when the correction process is finished.

The screw is made out of titanium alloy, which gives it a particular strength, and the patient can undergo magnetic examinations, if there is any need for such while the screw is implanted.

STATE OF THE ART

The techniques of the surgical method "Calcaneo stop" used thus far for correcting flat feet, used different screws which were placed into the already mentioned feet bone in anterograde (talus 8) and retrograde (calcaneus 9) direction. The resorptive screw, which is placed in the sinus 10, i.e in the gap between the mentioned bones.

While placing the already known screws one had to show the sinus, i.e. operative area to display the bones in which one would place the screws in the corrcect position. So far, the used screws were as follows:

The ordinari spongious screw, which is placed in talus 8 anterograde, breaks transversally in 5-10% of patients. Placing of the screw is not suffiecently correct if one does not open the operative area. Bad direction of the screw while positioning and placing it, happens in 4-9% of patients according to our and the analysis from the rest of the world. The head of the screw is round, so it sinks into the heel bone during the correction process and the effect of the correction of the axis of the heel bone (calcaneus 9) becomes over time smaller.

The Casteman screw is also placed anterograde in the talus 8 bone. The positioning, i.e. placing of the screw precisely is questionable (there is no directing of the screw), the same as in the ordinary spongious screw. The authors mention its premature loosening in 5-7% of patients. The screw's neck is conical and narrower than the screw-thread, so there is no effect of self-tigthtening, so the bone mass can grow into it, which could cause a problem when removing it.

The resorptive Giannini screw which is placed in the sinus 10, i.e. in the gap between the heel bone 9 and the talus bone 8, so it breaks regularily already after a year of its placement and slowly desintegrades, so the quality of the correction comes into question (it does not support the foot long enough in the corrective position), and we do not know sufficiently enough about the affects of the resorbed material. Some authors point out its premature loosening and falling out of the positioned place, so they do not recommend it.

The retrograde Nogarin screw, which is placed in the heel bone (calcaneus 9) retrograde, is also carried out by largely opening an operative area. The authors point out loosening of the srew in 5% of patients, and penetration of the same into the talus by 6% of the patients. This screw does not have a head, but a neck, which is narrower than the scew-thread, so the self-tightening cannot be achieved, therefore it penetrates into the talus bone easier.

SUMMARY OF THE INVENTION

The invented screw (implant) achieves complete correction (immediately) after the surgery. It is only necessary to make an incision into the skin of 8 mm (equal to the dimeter of the implant). The screw is directed through the incision, while the other tissue is simply pushed aside and not cut (like e.g. ligaments 13) so the screw could be positioned into its temporary place (talus bone 8). It is not necessary anymore to operatively open an area of 30-50 mm, i.e. harming the surrounding tissue. Because of its canulated shape 1, the invented implant can be easier correctly placed through a small gap in the skin (in a 3-D display) using the Kirschner's guide-wire while checking it with the fluorograph, not harming the cartilage nor the talus bone 8, if it is necessary to do several attempts to position the screw (implant) correctly.

The point 6 of the screw has an apex thread 2 which reduces the damage of the bone tissue. It allows the implant to go through easier, as well as the positioning in the bone.

The body 7 of the screw implanted is larger so it is more resistible to transverse breakage. If the implanted screw does break in time, it is much easier to remove it because of its canulated shape 1. The thread 5, whose edges 5a are wider and lean at the angle of 45°±25% reduce the loosening of the screw, which makes greater contact to the surface to the spongious bone, therefore a greater stability of the screw to transverse force.

The shape of the head 3 of the screw is conical. The spongious screw-thread 14 continues into the conical head 3 which is smooth to the top of the head of the screw. That makes the free movement of the calcaneus 9 bone in regard to the talus 8 bone while walking—i.e. the calcaneus 9 bone does not catch at the head 3 of the screw but it directs the bone gradually in the correct movement, i.e. position. The screw does not have a thin neck (the screws with the thin neck proved to break in 5-10% of patient) is much stronger. The conical head 3 which leads to the screw-thread 14 makes the self-tightening into the spongious bone possible and stops the premature loosening of the screw.

The conical head 3 does not allow the screw-thread 14 to grow into the cortical (strong) bone, so there are no problems when the implant/screw needs to be removed. The conical head 3 allows a permanent pressure on the heel bone 9 (during the period of the correction), not catching at the bone tissue (like other screws), therefore the implant does not make an imprint on the heel bone 9, i.e. it does not penetrate into the bone. This screw has the equal effect throughout the whole period of correction, i.e. three years. It is made out of titanium alloy, which is tougher, so it stops breakage of the screw in the area of insertion into the bone. It allows MR (magnetic resonance) examinations if there is need for one if another illnes appears.

DETAILED DESCRIPTION OF THE INVENTION EMBODIMENT

Figure 1:
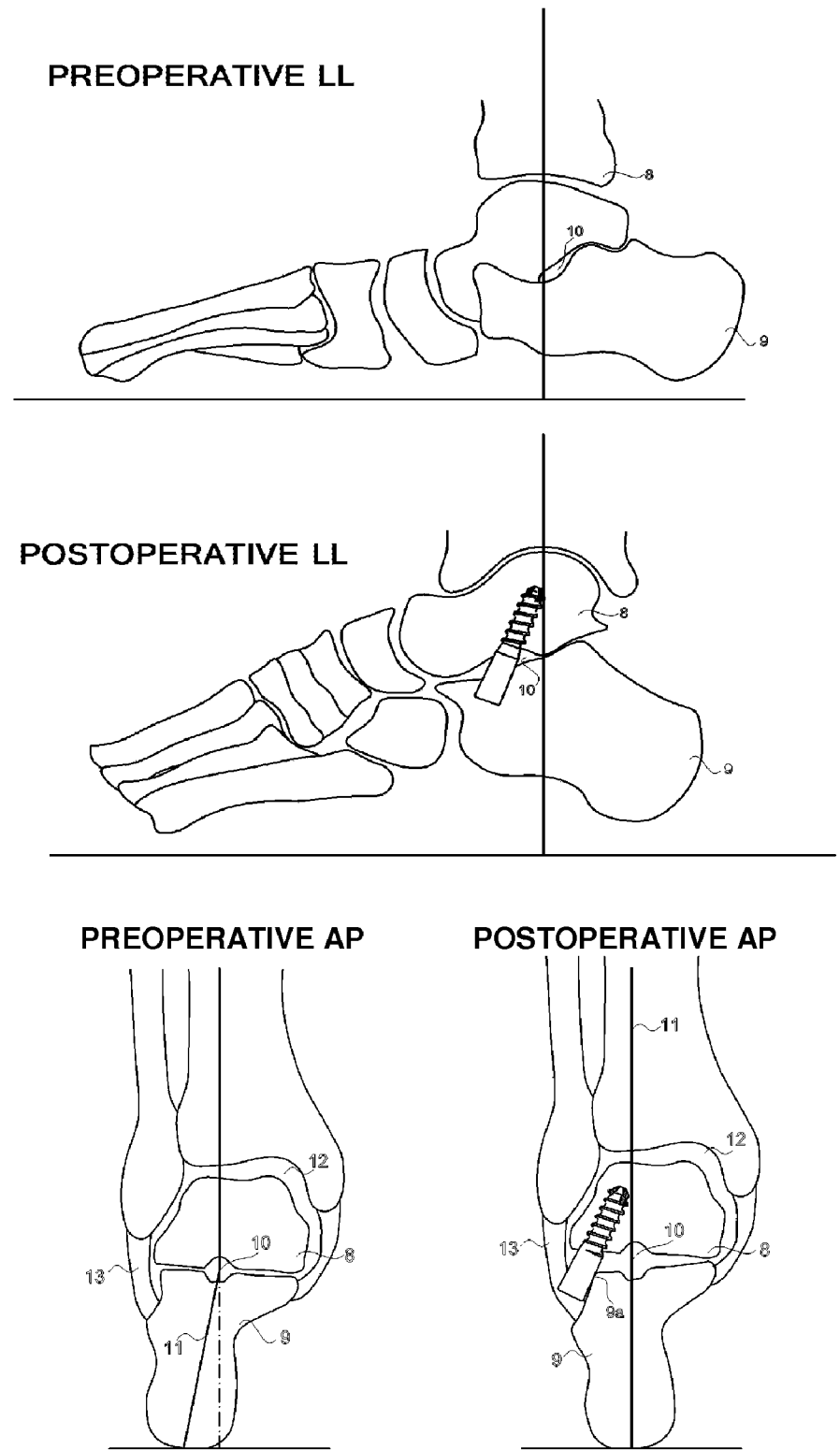
FIG. 1 shows the procedure of placing the screw into the talus 8 bone. It shows in which bone the screw is inserted, at which angle it is placed using the Kirschner's guide-wire and canulated imbus.

The placement of the screw and the procedure of insertion is clear from the previous pictures, as well as the instruments used for placing the screw. The screw is being used in treatment of painfully active correctable flat feet (3-4$^{th}$ stage) in children of the age 8-12 years, without plegia of the nervous system.

The screw is inserted as the patient undergoes general endotracheal anesthesia and removed under local anesthesia. After the pre-operative feet cleaning, a surgical incision of 8 mm is made into the skin. A band of fibrious tissue (fascia) is moved aside as well as the ligaments 13 lengthwise using small surgical scissors. The insertion position and the direction of the screw (implant) into the talus bone 8 is determined by using the drill and Kirscner's guide-wire, 1.8 mm in diametar, whose positioning is controlled by the fluorograph, which identifies the insertion place and the direction firstly of the guide-wire and then the screw into the talus bone 8, anterograde by 35° on the sagittal centerline plane and 45° on the frontal plane of the body. The length of the screw is determined by the other guide-wire, which is of the same length of the first guide-wire; then using the canulated drill, 4.5 mm thick, one makes an opening in the cortical bone then, one places the screw on the guide-wire and so using the canulated imbus spanner drills into the talus bone 8.

One checks the mobility of the foot ankle 12 and correction of the axis 11 of the heel bone 9 as well as the correction of the longitudinal arch of the foot. After that, one drills out the Kirschner's guide-wire. The ligaments 13 are repositioned, the band of the fibrious tissue (fascia) and the skin are closed each by one stich.

The patient can get up two days after the surgical procedure and walk, without using any immobilisation.

The screw stays implanted in the foot up to 30 months, depending on the age of the patient when the implant is first inserted.

It is removed, as one wishes, using local anesthesia. Meanwhile, the patient can take up sports without any obstacles.

There are 4 lengths 7 of the screw, which is made out of titanium alloy, which is placed depending on the need, i.e. the size of the feet bones, therefore the length 7 L (FIG. 2) is recommended:

25 mm±25%, recommended 25 mm±10%, and especially recommended 25 mm, 30 mm±25%, recommended 30 mm±10%, and especially recommended 30 mm, 35 mm±25%, recommended 35 mm±10%, and especially recommended 35 mm, 40 mm±25%, recommended 40 mm±10%, ane especially recommended 40 mm, With the change of the length 7 of the screw L, the length of the head 3 of the screw H is being proportionally changed (FIG. 2):

10 mm±25%, recommended 10 mm±10%, and especially recommended 10 mm, 12 mm±25%, recommended 12 mm±10%, and especially recommended 12 mm, 14 mm±25%, recommended 14 mm±10%, and especially recommended 14 mm, 16 mm±25%, recommended 16 mm±10%, and especially recommended 16 mm, The implant (screw), independently from the length 7 L, canulated by the tunnel 1 (FIG. 2) of the diameter C=2 mm±25%, recommended 2 mm±10% and especially recommended 2 mm.

The diameter of the screw stem 18 D (FIG. 2) is 4.8 mm±25%, recommended 4,8±10%, and especially recommended 4.8 mm.

The outer diameter of the screw-thread 19 E (FIG. 2) is 7.1 mm±25%, recommended 7.1 mm±10%, and especially recommended 7.1 mm.

The part of the screw with the screw-thread 14 continues directly into the conical head 3 (without the narrow neck 4) between the head 3 and the screw-thread 14.

The maximal diameter 20 of the conical head A (FIG. 2) is 8 mm±25%, recommended is 8 mm±10%, and especially recommended 8 mm.

The conical shape of the head 3 allows self-tightening into the bone in which the screw is inserted, which gives the screw stability as it is inserted. Therefore, the loosening as well as the breakage of the screw is minimal.

The conical part of the head 3 that leads into the stem 5 allows stemming against the bone on the larger surface of the screw, i.e. there is no osteolysis of the bone structure of the heel bone 9 on the pressure point 9a of the screw (because the pressure is lessened), so the correction is permanent and has the equal effect during the period of the screw is implanted.

The screw that has the step-like part between the head of the screw and the stem, has proven to catch at the edge of the heel bone 9 and therefore restrict the movement.

The invented screw does not restrict the movement from the moment it is placed and there on. The recess 16 of the hexagonal hole 17 in the screw head 3 (FIG. 2) for the imbus spanner is B=4.5 mm, and makes 4.5 mm±25%, recommended 4.5 mm±10%, especially recommended is 4.5 mm.

Figure 2:
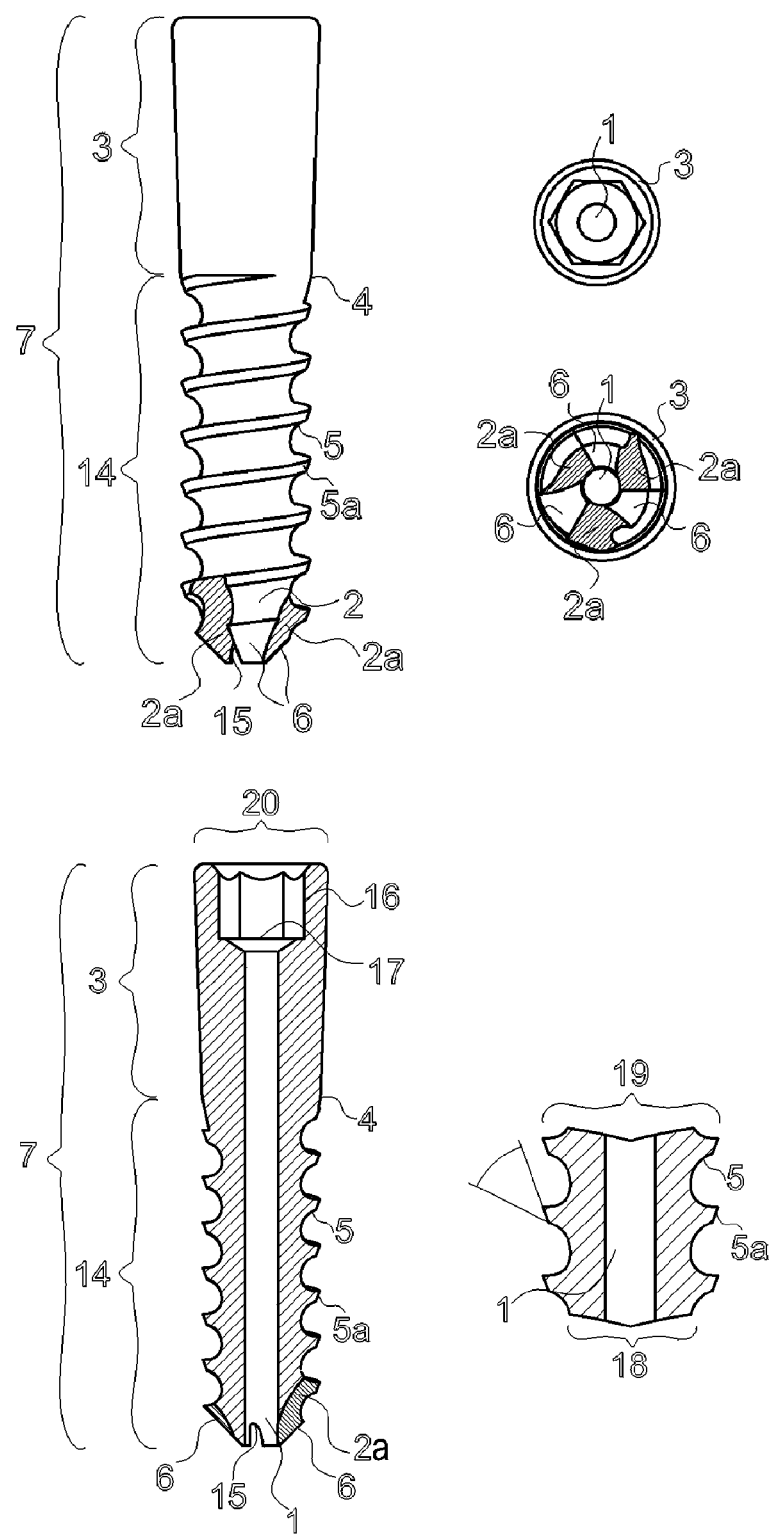
FIG. 2 shows the screw itself-technique data. There is a conical head 3 of the screw and its screw-thread 14 with the apex thread 2 on the point 6. The whole screw is canulated 1, so it can be easier directed.
Figure 3:
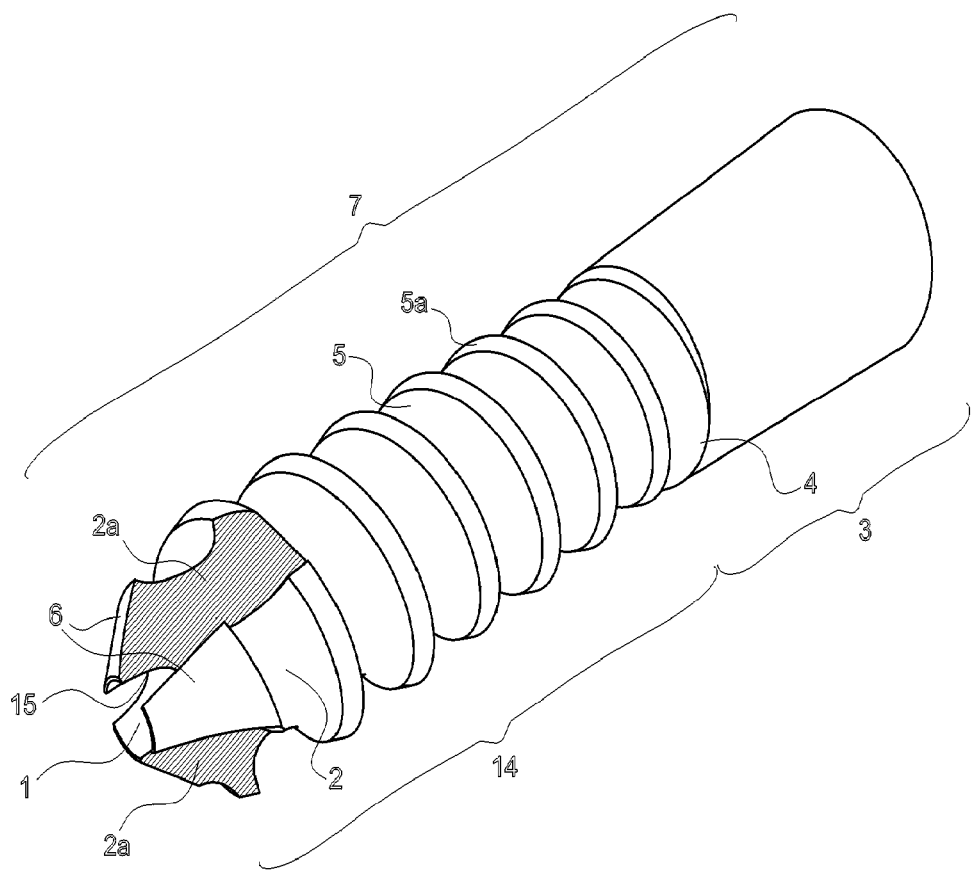
FIG. 3 shows the screw.
Figure 4:
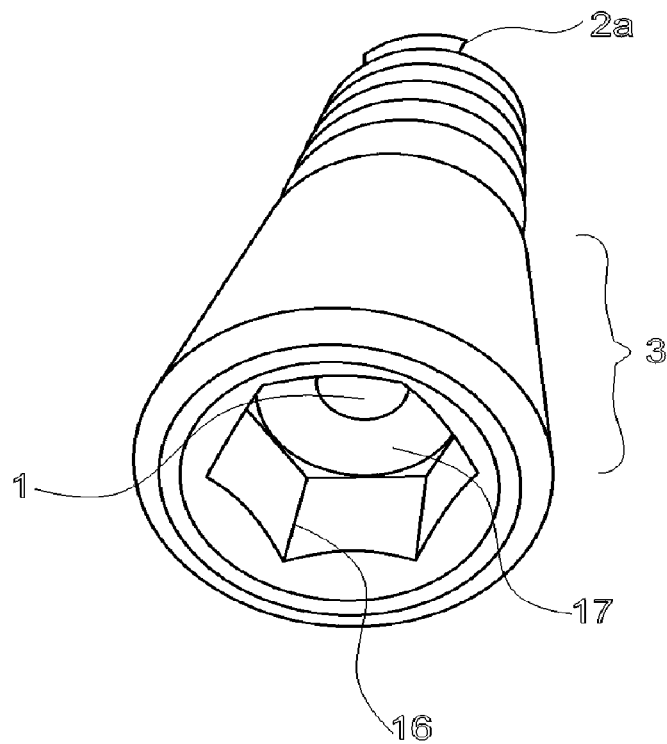
FIG. 4 shows the screw from its front and rear view.
Figure 4:
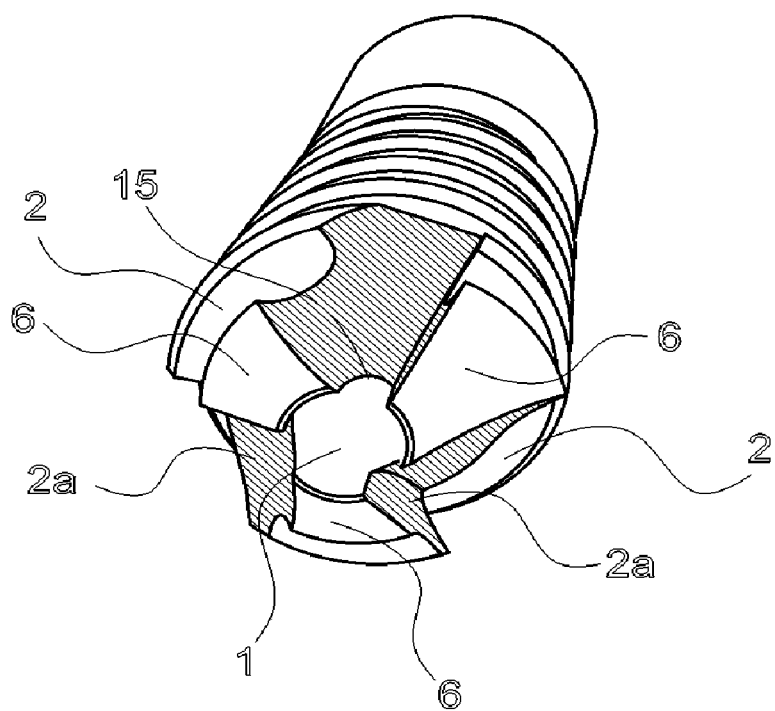

The screw-thread 14 has the usual ascent for the spongious bone by 2.7 mm (FIG. 2). Its edges 5a are thickened (FIG. 2). The edges 5a of the screw-thread finish at the angle Q=45°±25%, recommended 45°±10%, and especially recommended is 45°. This angle allows the thread edges 5a to lean on the spongious bone with grater surface, i.e. at the same diameter of the screw, a greater contact surfaces is achieved between the bone and the implant (screw), which allows greater stability to the transverse force, and therefore a lesser possibility of loosening. On the point 6 of the screw, which ends at the angle of 90°, on the apex thread 2 there are trisect cuts 2a at the angle of 120°. The edges of the apex thread 2 are cut at the angle of 55°. At the very top of the point 6 of the screw, the trisect cuts 2a of the apex thread 2 go inward the tunnel 15 in the length of the screw by 1.5 mm.

The invented implant (screw) is characterized by a simple-minimally invasive way of placement. Using the Kirschner's guide-wire of a diameter 1.8 mm, the screw's direction and the length is determined (35° on the sagittal centerline plane and 45° on the frontal plane anterograde). It is then inserted into the talus bone 8 with the imbus spanner. There are trisect cuts 2a on the apex thread 2, which authomaticlly exclude the usage of tapping device. Since there is no narrow part (neck) between head 3 and the screw-thread 14, the cortical bone does not arrest the screw. This makes removing of the screw after 3 years of correction easier and more simple.

THE USAGE OF THE INVENTION

The invented implant-screw makes the surgical procedure more simple and minimal invasive for the body and surrounding tissue. The post-operative duration is shortened as much as possible. The correction of the feet is complete and permanent.

Complications that arise, e.g. because of the bad positioning, loosening and/or breakage of the screw are minimal when compared to the already known methods and screws (implants). It allows a much higher percentage of satisfying post-operative results.

The possibility of post-operative infections are lesser as well, because the operative area is reduced. The patients can be examined by MR, while the screw is implanted, if such examination is necessary, because the screw is made out of titanium alloy. With other alloys this examination is forbidden.

The invention claimed is:

1. A canulated titanium implant for correction of flat feet in children, comprising:
   a screw-thread (14);
   a non-threaded smooth conical head (3) connected to the screw-thread, the conical head being free of any grooves extending along a conical surface thereof,
   the head (3) connected to the screw-thread free of any narrowing neck therebetween,
   the head comprising a tool recess (16),
   the screw-thread comprising a stem (18) and threads (5) extending from the stem, the stem and threads extending from the stem defining an overall cylindrical shape, the threads extending from the stem along an entire length of the screw-thread to the conical surface of the head, the conical head directly connected to the screw-thread;
   a self-drilling and self-tapping apex end point (6) terminating the stem configured to replace the use of a drill and tapping device; and
   a canulated tunnel extending through the head, the screw-thread, and the apex, wherein,
   a diameter of the head is 8.0 mm±25%,
   a diameter of the screw-thread is 7.1 mm±25%,
   a diameter of the stem is 4.8 mm±25%,
   a diameter of the tunnel is 2.0 mm±25%,
   a height of threads of the screw-thread is 1.15 mm±25%,
   the canulated titanium implant configured for correction of flat feet in children.

2. The canulated titanium implant according to claim 1, wherein,
   edges of an apex thread (2) have an angle of 55°, and trisect cuts (2a) extend into the tunnel 1.5 mm,
   edges of the threads of the stem have a thickened flat end surface at an angle of 45°±25%, and
   the end point ending at an angle of 90° with respect to an axis of the implant, the end point having the apex thread including the trisect cuts at an angle of 120°.

3. The implant according to claim 1, wherein,
   a length of the screw-thread and the conical head together is one of 25 mm±25%, 30 mm±25% 35 mm±25% and 40 mm±25%,
   a length of the conical head is one of 10 mm±25%, 12 mm±25%, 14 mm±25%, and 16 mm±25%, and
   the screw-thread and head are made of titanium alloy.

4. A canulated titanium implant for correction of flat feet in children, comprising:
   a first distal end defined by a self-tapping screw-thread (14);
   a second, opposite proximal end defined by a non-threaded smooth conical head (3) connected to the screw-thread, the conical head being free of any grooves extending along a conical surface thereof;
   the head comprising a hexagonal recess (16),
   the screw-thread having a threaded stem portion, the threads extending from the stem along an entire length of the screw-thread to the conical surface of the head, the conical head directly connected to the screw-thread, the threads ending in an angled thickened flat surface, the stem terminating in an apex end point (6), the end point having an apex thread (2) including trisect cuts (2a); and
   a canulated tunnel extending both through the head and the screw-thread, wherein,
   a diameter of the head is 8.0 mm±25%,
   a diameter of the screw-thread is 7.1 mm±25%,
   a diameter of the stem is 4.8 mm±25%,
   a diameter of the tunnel is 2.0 mm±25%,
   edges of the apex thread have an angle of 55°, and
   the angled flat surface of the threads of the stem have an angle of 45°±25%,
   the canulated titanium implant configured for correction of flat feet in children.

5. The implant of claim 4, wherein the head is connected to the screw-thread free of any narrowing neck therebetween.

6. The implant according to claim 5, wherein,
a length of the screw-thread and the head together is one of 25 mm±25%, 30 mm±25% 35 mm±25% and 40 mm±25%, and
a length of the conical head is one of 10 mm±25%, 12 mm±25%, 14 mm±25%, and 16 mm±25%, respectively.

7. The implant according to claim 6, wherein the screw-thread and head are made of titanium alloy.

8. The implant according to claim 6, wherein,
a diameter of the head is 8.0 mm,
a diameter of the screw-thread is 7.1 mm,
a diameter of the stem is 4.8 mm,
a diameter of the tunnel is 2.0 mm, and
the angled flat surface of the threads of the stem have an angle of 45°.

9. The implant according to claim 4, wherein, a length of the hexagonal recess is 4.5 mm±25%.

10. A canulated titanium implant for correction of flat feet in children, consisting essentially of:
a first distal end defined by a titanium alloy self-tapping screw-thread (14);
a second, opposite proximal end defined by a titanium alloy non-threaded smooth conical head (3) connected to the screw-thread, the conical head being free of any grooves extending along a conical surface thereof;
the head comprising a hexagonal recess (16),
the screw-thread having a threaded stem portion with an overall cylindrical shape, the threads extending from the stem along an entire length of the screw-thread to the conical surface of the head, the conical head directly connected to the screw-thread, the threads ending in an angled flat surface, the stem terminating in an apex end point (6), the end point having an apex thread (2) including trisect cuts (2a); and
a canulated tunnel extending both through the head and the screw-thread,
wherein the head is connected to the screw-thread free of any narrowing neck therebetween,
the canulated titanium implant configured for correction of flat feet in children.

11. The implant according to claim 10, wherein,
a length of the screw-thread and the head together is one of 25 mm±25%, 30 mm±25% 35 mm±25%, and 40 mm±25% respectively.

12. The implant according to claim 10, wherein,
a length of the conical head is one of 10 mm±25%, 12 mm±25%, 14 mm±25%, and 16 mm±25%.

13. The implant according to claim 10, wherein, a length of the hexagonal recess is 4.5 mm±25%.

* * * * *